United States Patent [19]

Frame

[11] Patent Number: 4,613,580
[45] Date of Patent: Sep. 23, 1986

[54] PROCESS FOR THE OLIGOMERIZATION OF OLEFINS AND A CATALYST THEREOF

[75] Inventor: Robert R. Frame, Glenview, Ill.

[73] Assignee: UOP Inc., Des Plaines, Ill.

[21] Appl. No.: 737,320

[22] Filed: May 23, 1985

[51] Int. Cl.$^4$ ............................................... C08F 4/70
[52] U.S. Cl. .................................. 502/117; 585/531; 585/521
[58] Field of Search ........................................ 502/117

[56] References Cited

U.S. PATENT DOCUMENTS

| | | | |
|---|---|---|---|
| 3,170,904 | 2/1965 | Ueda et al. | 260/94.3 |
| 3,483,269 | 12/1969 | Magoon et al. | 260/683.15 |
| 3,562,351 | 2/1971 | Mertzweiller et al. | 260/683.15 |
| 3,592,869 | 7/1971 | Cannell | 260/683.15 D |
| 3,644,564 | 2/1972 | van Zwet et al. | 260/683.15 D |
| 3,655,810 | 4/1972 | Chauvin et al. | 502/117 X |
| 3,661,995 | 5/1972 | Waddan et al. | 502/117 X |
| 3,663,451 | 5/1972 | Hill | 252/431 R |
| 3,679,772 | 7/1972 | Yoo | 260/680 B |
| 3,697,617 | 10/1972 | Yoo et al. | 260/683.15 D |
| 3,728,283 | 4/1973 | Chauvin et al. | 502/117 X |
| 3,736,308 | 5/1973 | Hashimoto et al. | 502/117 X |
| 3,755,490 | 8/1973 | Yoo et al. | 260/683.15 D |
| 3,954,668 | 5/1976 | Yoo et al. | 252/431 P |
| 4,000,211 | 12/1976 | Smith et al. | 502/117 X |
| 4,176,086 | 11/1979 | Carter | 502/117 X |

FOREIGN PATENT DOCUMENTS 1390530 4/1975 United Kingdom .

*Primary Examiner*—Patrick P. Garvin
*Attorney, Agent, or Firm*—Thomas K. McBride; John F. Spears, Jr.; Raymond H. Nelson

[57] ABSTRACT

Olefins may be oligomerized to a desired oligomer and configuration of the oligomer by utilizing a catalyst which comprises a porous support containing a catalytically effective amount of an hydrate of an iron group metal salt in which the mole ratio of water of hydration to iron group metal is greater than 0.5:1 in combination with a catalytically effective amount of an alkyl aluminum compound and an aluminum halide.

16 Claims, No Drawings

PROCESS FOR THE OLIGOMERIZATION OF OLEFINS AND A CATALYST THEREOF

BACKGROUND OF THE INVENTION

The oligomerization of olefins is known in the art, such oligomerization processes being effected by treating olefinic hydrocarbons with certain catalysts to obtain various oligomers which will find a useful function in the chemical art. One type of catalyst which may be employed for this particular type of reaction comprises a supported metal compound. For example, U.S. Pat. No. 3,562,351 discloses a method for dimerizing olefins utilizing a supported catalyst which has been prepared by impregnating a suitable support with a salt solution of a Group VIII metal followed by a heat treatment in an inert atmosphere at a temperature less than that which is required to form a metal oxide but which will form a complex on the surface of the solid support. Following this, the catalyst is activated by treatment with an organometallic compound. U.S. Pat. No. 3,483,269 describes a catalyst useful for oligomerizing lower olefins which comprises a $\pi$-allyl nickel halide supported on an acidic inorganic oxide support. If so desired, the support may have been optionally treated with an alkyl aluminum compound. U.S. Pat. No. 3,592,869 also describes a catalyst which is useful for the oligomerization of olefins. A divalent nickel compound and an alkyl aluminum compound are contacted with an olefinic compound. The resulting mixture is then used to impregnate an inorganic refractory oxide support. Another patent, namely U.S. Pat. No. 3,644,564, describes a catalyst for the oligomerization of ethylene which comprises an organo aluminum-free reaction product of a nickel compound which is an atom of nickel in complex with an olefinically unsaturated compound and a fluorine-containing ligand. The catalysts are typically formed in situ. U.S. Pat. No. 3,679,772 describes a process for reacting monoolefins with diolefins, the catalyst for such a reaction comprising a complex of (1) nickel, (2) a Group VA electron donor ligand such as an organophosphine, (3) a nonprotonic Lewis acid and (4) a reducing agent which itself may be a Lewis acid, all of which are composited on an acidic silica-based support.

U.S. Pat. No. 3,697,617 describes an oligomerization process involving the use of a catalyst comprising a complex of nickel with a chloro-containing electron donor ligand such as chlorodiphenylphosphine combined with a nonprotonic Lewis acid which is capable of forming a coordination bond with nickel and a reducing agent capable of reducing nickel acetylacetonate to an oxidation state less than 2. This complex may be composited on a solid support comprising an acidic silica-based material such as silica-alumina. The Lewis acid and the reducing agent may comprise the same compound as, for example, ethyl aluminum sesqui chloride. U.S. Pat. No. 3,663,451 describes a catalyst which is obtained by reacting a transition metal halide such as nickel halide with a carrier to give a carrier-metal bond. This product is then reacted with a ligand such as a phosphine or $\beta$ ketone and finally activated by treatment with an aluminum alkyl or chloro alkyl.

U.S. Pat. No. 3,755,490 describes the polymerization of an olefin utilizing a catalyst comprising nickel, a Group VA electron donor ligand, a Lewis acid, and a reducing agent on a solid acidic silica-based support. U.S. Pat. No. 3,954,668 is drawn to an oligomerization catalyst comprising a nickel compound, a chloro-containing electron donor ligand, or a phosphorous compound, a nonprotonic Lewis acid reducing agent which is capable of reducing nickel acetylacetonate to an oxidation state of less than 2 and which is also capable of forming a coordination bond with a nickel. U.S. Pat. No. 3,170,904 speaks to a catalyst which is useful for polymerization comprising a large surface area metal of Groups VIIA or VIII of the Periodic Table, boron trifluoride etherate, an organometallic compound of Groups I, II, III or IV or a halo derivative of an organometallic compound of Groups II, III or IV or a hydride of a metal of Groups I, II or III. The large surface area metal which comprises one component of this catalyst is in metallic form as, for example, Raney nickel. If so desired, the catalyst may be composited on a diatomaceous earth carrier. In like manner, U.S. Pat. No. 3,170,904 discloses a catalyst which comprises (A) a carrier-supported nickel or cobalt oxide which has been prepared by impregnating the carrier with the hydroxide, organic acid salt, inorganic acid salt, followed by oxidation in the presence of oxygen or a combination of nitrogen and oxygen; (B) a boron, titanium, zirconium, or vanadium halide; and (C) an alkyl metal or alkyl metal halide. In addition to these patents, British Patent No. 1,390,530 describes an oligomerization catalyst which has been prepared by thermally pretreating a metal oxide carrier material followed by reacting with a halogen-containing organo-aluminum compound and thereafter in a step-wise fashion, impregnating this product with a divalent nickel or cobalt complex at temperatures ranging from $-50°$ to $150°$ C.

As will hereinafter be shown in greater detail, the oligomerization of olefinic hydrocarbons may be accomplished by treating said olefins in the presence of a catalyst which has been prepared in a manner such that the catalyst will remain active and stable for a relatively long period of time and, in addition, will provide products which possess a desired configuration with respect to the branching or minimal branching of the chain.

BRIEF SUMMARY OF THE INVENTION

This invention relates to a catalytic composite which is useful for the oligomerization of olefinic hydrocarbons. More specifically, the invention is concerned with a catalyst composite and a process for the oligomerization of olefinic compounds, particularly olefinic hydrocarbons, whereby the use of the catalytic composite will result in the obtention of selective oligomers of the olefinic feed stock.

The term "polymerization" has a relatively broad meaning in the chemical art. Although it is generally referred to as the preparation of relatively high molecular weight polymers, that is polymers possessing molecular weights of greater than 50,000 or more, it may also refer to low molecular weight polymers, that is, polymers possessing molecular weights lower than 50,000. In contradistinction to this, the term "oligomerization" refers to polymeric compounds in which the molecules consist of only a relatively few monomeric units and thus would include dimerization, trimerization or tetramerization.

Many olefinic hydrocarbons which contain from 4 to about 12 carbon atoms in the chain are utilized in various industries in many ways. For example, dimers of propylene regardless of the amount of branching may be used to improve the octane number of motor fuels which are utilized in internal combustion engines utilizing gasoline as the fuel thereof. The presence of these compounds in a motor fuel such as gasoline will improve the octane number of the fuel to a high level, thus enabling the gasoline to be utilized in combustion engines in an unleaded state. Other uses for dimers containing 6 carbon atoms would be in the synthesis of flavors, perfumes, medicines, dyes and resins. Another use of an oligomer would be found in the dimerization product of butene in which the dimer which possesses a relatively straight chain configuration with a minimum of branching such as one methyl substituent on the chain would be as an intermediate in the production of a plasticizer. The plasticizer, when added to a plastic will facilitate compounding and improve the flexibility as well as other properties of the finished product. Likewise, a trimer of butene or a dimer of hexene in which the olefin contains 12 carbon atoms may be used as an intermediate in various organic syntheses such as in the preparation of detergents, lubricants, additives, plasticizers, flavors, perfumes, medicines, oils, dyes, etc. In addition, linearized oligomers containing 12 or more carbon atoms, upon hydrogenation, provide excellent diesel fuels.

It is therefore an object of this invention to provide a catalyst for the oligomerization of olefinic hydrocarbons.

A further object of this invention is to provide a specific catalyst system which may be used in a process for the oligomerization of olefinic hydrocarbons whereby selective oligomers may be obtained thereby.

In one aspect an embodiment of this invention resides in a catalytic composite comprising a combination of a catalytically effective amount of an alkyl aluminum compound on a porous support containing a catalytically effective amount of hydrate of an iron group metal salt in which the mole ratio of water of hydration to iron group metal is greater than 0.5:1.

Another embodiment of this invention is found in a process for the oligomerization of an olefinic hydrocarbon which comprises treating said hydrocarbon in the presence of a catalyst comprising a combination of a catalytically effective amount of an alkyl aluminum compound composited on a porous support containing a catalytically effective amount of hydrate of an iron group metal salt in which the mole ratio of water of hydration to iron group metal is greater than 0.5:1, at oligomerization conditions, and recovering the resultant oligomer.

A specific embodiment of this invention is found in a catalytic composite comprising a combination of a catalytically effective amount of diethyl aluminum chloride on an alumina support which contains a catalytically effective amount of nickel hydrate, the mole ratio of water of hydration to iron group metal being in a range of from about 0.5:1 to about 6:1 prior to reaction with said diethyl aluminum chloride, said diethyl aluminum chloride being present in a mole ratio in the range of from about 0.05:1 to about 6:1 moles of diethyl aluminum chloride per mole of nickel.

Another specific embodiment of this invention is found in the process for the oligomerization of an olefinic hydrocarbon which comprises treating propylene in the presence of a catalyst comprising a combination of a catalytically effective amount of diethyl aluminum chloride on an alumina support which contains a catalytically effective amount of nickel hydrate, the mole ratio of water of hydration to iron group metal being in a range of from about 0.5:1 to about 6:1 prior to reaction with said diethyl aluminum chloride, said diethyl aluminum chloride being present in a mole ratio in the range of from about 0.05:1 to about 6:1 moles of diethyl aluminum chloride per mole of nickel at a temperature in the range of from about $-20°$ to about $120°$ C. and a pressure in the range of from about 350 to about 1000 pounds per square inch gauge, and recovering the resultant oligomer comprising a mixture of hexene, methylpentene and dimethylbutene.

Other objects and embodiments will be found in the following detailed description of the invention.

DETAILED DESCRIPTION OF THE INVENTION

As hereinbefore set forth, the present invention is concerned with a catalyst composite which may be utilized for the oligomerization of olefins and to a process which employs the catalyst. Heretofore, the preparation of a catalytic composite which may be used for the polymerization or oligomerization of olefinic compounds was relatively difficult inasmuch as several relatively expensive compounds were required as components of the composite. In contradistinction to this, the catalytic composite of the present invention is relatively easy to prepare and, in addition, employs compounds which are less expensive than the components of the other catalyst. The final catalytic composite of the present invention will possess a high activity and will be stable over a relatively long period of time. In addition to these desired attributes, the catalyst will also produce a high yield of dimer products, especially from $C_3$ and $C_4$ olefins as compared to trimer and tetramer products. The dimer products produced by the oligomerization of propylene or the n-butenes will possess a high percentage of linear compounds, that is, n-hexenes and n-octenes and also a high percentage of dimers which contain only one methyl substituent; more highly branched oligomers being minority products. The propylene dimers which are produced by the process of the present invention all possess high octane numbers regardless of the branching, and thus are excellent octane blending components. In addition, the n-butene dimers are excellent as intermediates in the preparation of plasticizers.

The catalytic composite of the present invention will comprise a combination of a catalytically effective amount of an alkyl aluminum compound on a porous support which contains a catalytically effective amount of hydrate of an iron group metal salt. In addition, if so desired, the catalytic composite can also contain, in combination therewith, a catalytically effective amount of an aluminum halide. In the preferred embodiment of the invention, the hydrate of an iron group metal salt will be obtained from a soluble salt of nickel or cobalt such as, for example, nickel nitrate, nickel hydroxide, nickel bromide, nickel chloride, nickel fluoride, nickel acetate, cobaltic chloride, cobaltus acetate, cobaltus ammonium chloride, cobaltus bromide, cobaltus fluoride, cobaltus perchlorate, cobaltus sulfate, etc. The porous support upon which the iron group metal hydrate is impregnated will include inorganic metal oxides such as alumina, silica, mixtures of oxides such as alumina-silica, alumina-zirconia-magnesia, etc. or crystalline aluminosilicates which are commonly known as zeolites.

The other components of the catalytic composite will comprise alkyl aluminum compounds such as dimethyl aluminum chloride, diethyl aluminum chloride, dipropyl aluminum chloride, dimethyl aluminum bromide, diethyl aluminum bromide, dipropyl aluminum bromide, dimethyl aluminum iodide, diethyl aluminum iodide, dipropyl aluminum iodide, etc. In addition, the aluminum halide which may be used to form a component of the catalytic composite in conjunction with the alkyl aluminum compound will include aluminum chloride, aluminum bromide, aluminum iodide, etc. It is to be understood that the aforementioned list of iron group metal compounds, porous supports, alkyl aluminum compounds and aluminum halides are only representative of the class of compounds which may be employed to form the catalytic composite of the present invention, and that said invention is not necessarily limited thereto.

The oligomerization catalyst of the present invention may be prepared in such a manner so as to provide the finished catalyst with certain characteristics with regard to the selectivity of olefins obtained by the reaction of an olefin in the presence of said catalyst as well as a specificity of the product so obtained. The catalyst composite is prepared by impregnating a porous support of the type hereinbefore set forth with a simple divalent iron group metal salt such as, for example, nickel nitrate, preferably from an aqueous solution. After impregnation of the porous support such as alumina, which is effected at ambient temperature and atmospheric pressure, the impregnated support is then subjected to a thermal treatment. By varying the temperature of the thermal treatment, it is possible to obtain a catalyst composite which will provide a greater selectivity to dimer products resulting from the oligomerization of the olefin in contrast to trimer and tetramer products than are obtained when using other conventional oligomerization catalysts. The thermal treatment of the impregnated support is preferably effected in a range of from about 350° to about 450° C., the preferred thermal treatment temperature being in a range of from about 340° to about 360° C. The thermal treatment of the catalyst base containing the impregnated iron group metal salt in hydrate form will result in a weight loss due to a loss of water of hydration from the metal salt. In the preferred embodiment of the invention, the mole ratio of water of hydration to iron group metal following the thermal treatment will be greater than 0.5:1 and preferably in a range of from about 0.5:1 to about 6:1.

Following the thermal treatment, the iron group metal impregnated catalyst base is then treated with an alkyl aluminum compound wherein the activated solution will produce a catalyst of maximum activity. The treatment of the base with the activating agent is also effected at ambient temperature and atmospheric pressure utilizing a solution of the alkyl aluminum compound dissolved in an organic solvent such as benzene, toluene, the xylenes, etc. In the preferred embodiment of the invention, in addition to the alkyl aluminum compound which may be of the type hereinbefore set forth in greater detail, an aluminum halide compound may also be used in this step. The addition of the impregnated base to the organic solution will result in an exothermic reaction and after thorough admixture, the solution is allowed to return to room temperature. The solvent may then be removed by conventional means such as decantation, evaporation, etc. and the catalyst thereafter washed with an organic solvent to remove residue or trace portions of unwanted compounds. Thereafter, the catalyst may then be dried by purging with nitrogen, and recovered. In the finished composite, the alkyl aluminum compound is present in the composite in a mole ratio in the range of from about 0.05:1 to about 6:1, preferably in a range of from about 0.1:1 to about 1:1, moles of alkyl aluminum compound per mole of iron group metal, the latter being present in said composite, on an elemental basis, in an amount in the range of from about 1% to about 20% by weight of the composite, and preferably in an amount in a range of from about 1% to about 10%.

As will hereinafter be shown in greater detail, by preparing a catalyst which possesses the various components in the finished composite in mole ratios or weight percent within the ranges hereinbefore set forth, it is possible to selectively oligomerize olefin compounds containing from about 2 to about 6 carbon atoms with a concurrent obtention of desirable isomers in each of the oligomer products. In addition, by utilizing an aluminum halide as a component of the catalyst composite in addition to the alkyl aluminum compound, it is possible to obtain a catalyst composite which will be more stable and more active in the conversion of olefins to oligomers than are catalysts which do not contain this compound.

As an example of how the catalyst composite of the present invention may be prepared, a predetermined amount of a porous base such as alumina, silica, silica-alumina, aluminosilicate, etc. which may be in the form of spheres, pellets, rods, etc. may be prepared in an appropriate apparatus such as an evaporator along with an aqueous solution of a hydrated salt of an iron group metal. The mixture may be thoroughly admixed and following this, the apparatus heated to form the desired iron group metal impregnated base. The impregnated base may then be placed in a heating apparatus such as a tube furnace and treated with air while bringing the catalyst to a temperature of about 250° C. The heating is accomplished at a relatively slow rate and after the determined temperature has been reached, it is maintained thereat for an additional period of time which may range from about 2 to about 4 hours or more in duration. The calcination of the catalyst base is then effected by increasing the temperature to a predetermined level and maintaining thereat for a period of time sufficient to bring the mole ratio of water of hydration present in the iron group metal salt to a determined level which is preferably in an excess of about 5:1 moles of water of hydration per mole of iron group metal.

After allowing the calcination to proceed for this predetermined period of time, heating is discontinued and the catalyst base which contains from about 1% to about 20% by weight of iron group metal is allowed to cool. The cooled base may then be admixed with a solution of an alkyl aluminum compound and an aluminum halide dissolved in an organic solvent. As previously discussed, the resulting reaction is exothermic in nature and after allowing the heat to dissipate, the resulting admixture is thoroughly stirred and allowed to stand for a period of time which may range from about 1 to about 100 hours or more in duration. At the end of this period, the organic solvent is removed by decantation, filtration, centrifugation, etc. and the solid catalyst is washed to remove any unreacted material. After washing, the catalyst is then dried in an inert atmosphere such as that provided for by the presence of nitrogen, and recovered.

The oligomerization of olefins containing from 2 to about 6 carbon atoms such as ethylene, propylene, butene-1, butene-2, pentene-1, pentene-2, pentene-3 may then be effected by treating the oligomer in the presence of the catalyst at oligomerization conditions which will include a temperature in the range of from about −20° C. to about 120° C., the preferred range being from about 30° to about 80° C., and a pressure in the range of from about 350 to about 1000 pounds per square inch gauge (psig). The pressure which is utilized may be the autogenous pressure provided for by the feedstock, if in gaseous phase, or, the feedstock may supply only a partial pressure, the remainder of said pressure being provided by the introduction of an inert gas such as nitrogen, helium, argon, etc. into the reaction zone.

It is contemplated within the scope of this invention that the oligomerization process may be effected in either a batch or continuous type operation. For example, when a batch type operation is employed, a quantity of the novel catalyst composite of the present invention may be placed in an appropriate apparatus such as, for example, an autoclave of the rotating, mixing or stirring type. If the olefinic feedstock is in gaseous form, the autoclave is sealed and the feedstock comprising the olefinic hydrocarbon or a mixture of olefinic and paraffinic hydrocarbon or similar carbon atom length are charged to the reactor until the desired operating pressure has been attained. The apparatus is then heated to the desired operating temperature and maintained thereat for a predetermined period of time which may range from about 1 to about 6 hours or more in duration. At the end of this period of time, heating is discontinued and after the apparatus and contents thereof have returned to room temperature, the excess pressure is discharged and the autoclave is opened. The reaction product is recovered, separated from the catalyst by conventional means such as decantation, filtration, centrifugation, etc. and, if so desired, subjected to fractional distillation whereby the various isomers may be separated, one from another, and stored. Conversely, if so desired, the reaction product comprising a mixture of isomers may be recovered and stored per se without separating the various isomeric fractions which are present in the product mixture.

In the event that the olefinic charge stock is in liquid form, it may be charged to the reactor which is thereafter sealed and pressured to the desired operating pressure by the introduction of an inert gas of the type hereinbefore set forth. The remainder of the operations to obtain the desired oligomer product is carried out in a manner similar to that previously described.

When utilizing a continuous method of operation to obtain the desired oligomer products, a quantity of the catalyst composite is placed in an appropriate apparatus. The feedstock comprising the olefinic compound is continuously charged to this reactor which is maintained at the proper operating conditions of temperature and pressure. As in the case of the batch type operation, the desired operating pressure may be provided for by the olefinic hydrocarbon itself or by the addition of a heated inert gas. After passage through the reactor for a predetermined period of time, the reactor effluent is continuously discharged and the reaction product may be recovered and passed to storage or it may be passed to a distillation apparatus whereby separation of the various isomers and oligomers may be effected. Any unreacted olefinic hydrocarbon which is recovered from the reactor effluent may be recycled back to the reactor to form a portion of the feed charge.

Inasmuch as the catalyst composite of the present invention is in solid form, the continuous method of operation for obtaining the desired oligomers of the olefinic hydrocarbons may be effected in various types of operations. For example, in one type of operation, the catalyst is positioned as a fixed bed in the reaction zone and the olefinic feedstock is charged so that it passes over the catalyst bed in either an upward or downward flow. Another type of continuous operation which may be employed comprises the moving bed type of operation in which the catalyst bed and the feedstock are passed through the reaction zone either concurrently or countercurrently to each other. In addition to the fixed or moving bed type of operation, it is also contemplated that the slurry type of operation may be employed, especially when the olefinic hydrocarbon feedstock is in liquid form. When this type of operation is employed, the catalyst is charged to the reactor as a slurry in the olefinic feedstock.

Examples of oligomers of olefinic compounds which may be obtained when utilizing the catalyst composite of the present invention will include n-butene, isobutene, n-hexene, methyl pentene, dimethyl butene, n-octene, the isomeric heptenes, dimethyl hexenes, n-dodecene, the isomeric methyl undecenes, dimethyl decenes, etc. As was previously stated, the oligomer products which are obtained in the process of this invention will comprise, in the main, the dimers of the particular olefinic compound which was employed as the feedstock, thus, for example, when employing ethylene as the feed, the reaction product will comprise mostly $C_4$ olefins; when employing propylene as the feedstock, the reaction product will comprise mostly $C_6$ olefins; and when employing butene as the feedstock, the reaction product will comprise mostly $C_8$ olefins. Thus, the catalyst composite of the present invention will result in products which find particular uses in the finished product.

The following examples are given for purposes of illustrating the novel catalyst composites of the present invention, methods for preparing these composites and a process for utilizing these composites. However, it is to be understood that these examples are merely illustrative in nature and that the present invention is not necessarily limited thereto.

EXAMPLE I

A catalyst was prepared by impregnating 250 cc of alumina spheres with an aqueous solution of 250 cc of water containing 34.6 grams of nickel nitrate hexahydrate. The impregnation was effected in a rotary evaporator in which the mixture was rolled for a period of 0.5 hours with no heat. The evaporator was then heated with steam for a period of two hours at which time the water phase was evaporated. The catalyst base was then loaded into a tube furnace and air was passed through the catalyst bed at a rate of 600 cc per minute. Following this, the temperature of the bed was raised to 250° C. during a period of two hours and thereafter the bed was maintained at this temperature for an additional period of three hours. At the end of this time, the bed was allowed to cool to room temperature and thereafter the bed was calcined by raising the temperature to 400° C. during a two-hour period. The 400° C. calcination temperature was maintained for an additional period of three hours following which heating was discontinued and the impregnated base was recovered.

An activating solution was prepared by adding 3.91 grams of anhydrous aluminum chloride to 174 cc of toluene in a 500 cc flask along with 18 grams of diethyl aluminum chloride as a 50 weight percent solution in toluene. The addition of the solutions was accomplished in a glove box while maintaining a nitrogen atmosphere for the addition. After thorough admixture, the solution was allowed to stand for a period of 3.5 hours with intermittent swirling thereof.

The impregnated base was placed in a 500 cc flask along with 240 cc of toluene. The activating solution containing the aluminum chloride and diethyl aluminum chloride was slowly added during a period of 15 minutes to avoid overheating of the catalyst due to the exothermic nature of the reaction. After addition of the activating solution to the support, the resulting solution was slightly warm with a concurrent emission of some gas bubbles. The solution was allowed to stand for a period of 18.5 hours at the end of which time the impregnated liquors were decanted and the catalyst was washed with six portions of isopentane utilizing 100 to 115 cc per wash. The resulting catalyst composite was then allowed to dry in a glove box under nitrogen atmosphere until it became free-flowing. This catalyst was designated as "A."

EXAMPLE II

A second catalyst composite was prepared in a manner similar to that set forth in Example I above. The catalyst base comprised 250 cc of alumina containing 5% by weight of nickel, said impregnated base again being calcined at a temperature of 400° C. The catalyst support was placed in a 500 cc flask along with 250 cc of toluene. A solution prepared in a manner similar to that set forth in Example I above from 18 grams of diethyl aluminum chloride as a 50 weight percent solution in toluene and 174 cc of toluene (no aluminum chloride being present) was slowly added during a period of 15 minutes to prevent overheating of the catalyst. Again, it was noted that the solution was slightly warm following the addition with the evolution of some gas bubbles. The solution was again allowed to stand for a period of 18.5 hours following which the impregnation liquors were decanted and the solid catalyst washed with six portions of isopentane using 115 to 120 cc per wash. This catalyst was then allowed to dry in a glove box under nitrogen until it was free-flowing in nature. The catalyst was designated as "B."

EXAMPLE III

The catalysts prepared according to the methods set forth in Examples I and II above were utilized in the oligomerization of butene-1. The oligomerization was effected by placing 100 cc of the catalysts in a tubular reactor having an outside diameter of 0.5". A feedstock comprising a mixture of 60% butene-1 and 40% n-pentane was charged to the reactor at a LHSV of 1.0 hours$^{-1}$ based upon the olefin. Reaction conditions which were employed for the oligomerization included a reactor inlet temperature of 35° C. and a pressure of 700 psig. The oligomerization was allowed to proceed for a period of 100 hours, samples being taken and analyzed at various points during the reaction period. The results of these analyses are set forth in Table 1 below:

TABLE 1

| Hours | Catalyst A | Catalyst B |
|---|---|---|
| | Unreacted Olefin % | |
| 20 | — | 28 |
| 30 | 11.5 | — |

TABLE 1-continued

| Hours | Catalyst A | Catalyst B |
|---|---|---|
| 55 | 12.5 | 31.5 |
| 75 | 12.0 | — |
| 80 | — | 32.5 |
| 100 | 13.0 | 37.5 |
| | Butene Conversion % | |
| 30 | 93 | 79 |
| 55 | 92 | 73 |
| 80 | 93 | 71 |
| 100 | 91 | 69 |

EXAMPLE IV

To illustrate the difference in selectivity factors which may be obtained by calcining the impregnated catalyst base at various temperatures, three different catalysts were prepared. The calcination of the alumina base was effected in a manner similar to that set forth in Example I above utilizing a nickel nitrate hydrate solution which resulted in a base containing 5% by weight of nickel. After drying the impregnated base at a temperature of 250° C. for a period of three hours, the base was then calcined by raising the temperature at which each base was calcined to different levels. After calcining the bases at the different temperatures, the bases were then treated with an activating solution of diethyl aluminum chloride and aluminum chloride in a manner also similar in nature to that set forth in Example I above to prepare the three finished catalyst composites.

The three catalyst bases were calcined at temperatures of 350°, 400°, and 450° C. respectively, the finished catalyst composites which resulted from the use of these bases being labeled C, D and E respectively. The finished catalyst composites were then utilized in an oligomerization reaction involving a feedstock comprising 60% butene-2 and 40% n-butane, said reaction being effected at a reactant inlet temperature of 70° C., a pressure of 700 psig and an olefin LHSV of 0.6 for C and 1.0 for D and E hrs.$^{-1}$.

The weight loss which each catalyst base underwent during the calcination period as well as the selectivity to isomeric octenes at a conversion rate of 50% of the butene-2 are set forth in Table 2 below:

TABLE 2

| | Catalyst | | |
|---|---|---|---|
| | C | D | E |
| Calcination Temp. °C. | 350 | 400 | 450 |
| Wt. Loss % | 2.9 | 1.5 | 0.8 |
| $C_8^=$ Selectivity | 88 | 76 | 54 |

It is apparent from the above Table that the temperature at which the impregnated catalyst base is calcined will have an effect upon the selectivity of the olefin oligomerization process, the lower calcination temperature providing the greatest percentage of selectivity.

In like manner, it is also evident from the results obtained when using two catalysts, one of which did not contain an aluminum halide as one component thereof, that a catalyst composite comprising a combination of a catalytically effective amount of an alkyl aluminum compound and an aluminum halide on a porous support which contains a catalytically effective amount of an iron group metal hydrate will result in obtaining a greater amount of oligomer than will be obtained when utilizing a catalyst which does not contain the aforesaid aluminum halide.

EXAMPLE V

An oligomerization catalyst was prepared by impregnating 250 cc of alumina spheres with an aqueous solution of 250 cc of water containing 34.6 grams of nickel nitrate hexahydrate. The impregnation was effected in a rotary evaporator in which the mixture was rolled for a period of 0.5 hours without heating, followed by heating with steam for a period of two hours at which time the water was evaporated. The catalyst base was then calcined in a manner set forth in the above example by loading into a tube furnace, heating to 250° C. for a period of two hours, cooling to room temperature followed by raising the temperature to 400° C. and maintaining the temperature for a period of three hours.

An activating solution was prepared by adding 1.5 grams of anhydrous aluminum chloride to 62 grams of toluene in a 500 cc flask along with 5.45 grams of diethyl aluminum chloride in 33 cc of hexane. The addition of the solutions was effected in a glove box while maintaining a nitrogen atmosphere and after thorough admixture, the solution was allowed to stand for a period of 3.5 hours.

To prepare the desired catalyst, 125 cc of the catalyst base was placed in a 500 cc flask along with 125 cc of toluene. The activator solution was then slowly added to the catalyst base over a period of 30 minutes in order to avoid overheating. The solution was warm and in addition, gas bubbles were formed after the addition. After allowing the solution to stand for a period of 18 hours, the solvents were decanted and the catalyst was washed with six 80 cc portions of isopentane. The catalyst composite was allowed to dry in a glove box under a nitrogen atmosphere and designated as "F."

EXAMPLE VI

In this example, 250 cc of alumina spheres were impregnated with an aqueous solution of 250 cc of water containing 34.6 grams of nickel nitrate hexahydrate in a manner similar to that set forth in Example V above. The catalyst base was then divided into six separate portions, loaded into a tube furnace, and treated in a manner similar to that set forth in the above example by calcining at a temperature of 400° C. for a period of three hours.

Six batches of activating solution were prepared by adding 3.9 grams of anhydrous aluminum chloride and 16.9 grams of diethyl aluminum chloride as a 50 wt. % solution and 39 cc of toluene to 174 cc of toluene. The mixing was effected in a glove box under a nitrogen atmosphere and after 3.5 hours all of the solid had dissolved. Each batch of the solution was used to activate the six 250 cc catalyst bases prepared according to the above paragraph. Each portion of the catalyst base was placed in a 500 cc flask along with 250 cc of toluene, the addition of the activator solution being accomplished over a 15 minute period. After allowing the solution to stand for a period of 18.5 hours, the solvent was decanted and each catalyst was washed with six 100-115 cc portions of isopentane. Thereafter, the catalyst portions were allowed to dry in a glove box under nitrogen and combined, this catalyst being designated "G."

EXAMPLE VII

To vary the ratio of nickel to aluminum halide, a catalyst was prepared by impregnating 250 cc of alumina spheres with an aqueous solution comprising 250 cc of water containing 71.3 grams of nickel nitrate hexahydrate. After impregnation, the catalyst base was treated in a manner similar to that hereinbefore set forth and loaded into a tube furnace during which air was passed through the catalyst bed at a rate of 600 cc per minute. Following this, the temperature of the bed was raised to 250° C. during a period of two hours and maintained thereat for an additional period of three hours. At the end of this time, the bed was allowed to cool to room temperature and thereafter, the catalyst was calcined by raising the temperature of the furnace to 350° C. during a two-hour period. The 350° C. calcination temperature was maintained for an additional period of two hours following which heating was discontinued and the impregnated base was recovered.

An activating solution was prepared by adding 5.87 grams of anhydrous aluminum chloride to 80 cc of toluene in a 500 cc flask along with 58.1 cc of a 50 wt. % diethyl aluminum chloride in a toluene solution (27.0 grams of diethyl aluminum chloride). A portion (125 cc) of the impregnated catalyst base was then placed in a 500 cc flask along with 120 cc of toluene. The activating solution was slowly added during a period of 15 minutes and allowed to stand for 18.5 hours. At the end of this time, the impregnating liquors were decanted and the catalyst was washed with six portions of isopentane utilizing 100 to 115 cc per wash. The catalyst composite was allowed to dry in a glove box under a nitrogen atmosphere until it became free-flowing, this catalyst being designated "H."

EXAMPLE VIII

Catalysts F, G and H which were prepared according to the above examples were used in a propylene oligomerization test. Each catalyst in an amount of 50 cc was placed in a tube reactor and a charge comprising 90% by weight of propylene and 10% by weight of propane was charged to each reactor at olefin Liquid Hourly Space Velocities ranging from 2.0 to 3.0 hours$^{-1}$. The reactors were maintained at a pressure of 700 pounds per square inch gauge while the bath temperatures were maintained at from 35° to 50° C. A fractionation column was used to separate unreacted $C_3$'s from the oligomers and a portion of the unreacted $C_3$'s (both propylene and propane) was recycled to the reactor inlet. The results of the runs are set forth in Table 3 below:

TABLE 3

|  | Catalyst "F" | Catalyst "G" | Catalyst "H" |
| --- | --- | --- | --- |
| Run Length (hrs.) | 1385 | 1042 | 36 |
| Overall Propylene Conversion (wt. %) | 88.7–99.8 | 92.6–99.9 | 61.3–91.7 |
| $C_6^=$ selectivity (wt. %) | 70.7–81.5 | 77.4–92.6 | — |
| Research Octane No. | 95–96 | 95–96 | — |
| Motor Octane No. | 80–81 | 80–81 | — |

I claim as my invention:

1. A catalytic composite comprising a combination of a catalytically effective amount of an alkyl aluminum compound on a porous support containing a catalytically effective amount of hydrate of an iron group metal salt in which the mole ratio of water of hydration to iron group metal is greater than 0.5:1.

2. The catalytic composite as set forth in claim 1 further characterized in that said composite contains in combination therewith a catalytically effective amount of an aluminum halide.

3. The catalytic composite as set forth in claim 1 in which said iron group metal is present in said composite, on an elemental basis, in an amount in the range of from about 1% to about 20% by weight of said composite.

4. The catalytic composite as set forth in claim 1 in which said alkyl aluminum compound is present in said composite in a mole ratio in the range of from about 0.05:1 to about 6:1 moles of alkyl aluminum compound per mole of iron group metal.

5. The catalytic composite as set forth in claim 1 in which the mole ratio of water of hydration to iron group metal in said hydrate of an iron group metal salt is in a range of from about 0.5:1 to about 6:1 prior to reaction with said alkyl aluminum compound.

6. The catalytic composite as set forth in claim 3 in which said iron group metal is nickel.

7. The catalytic composite as set forth in claim 3 in which said iron group metal is cobalt.

8. The catalytic composite as set forth in claim 1 in which said alkyl aluminum compound comprises an alkyl aluminum halide.

9. The catalytic composite as set forth in claim 8 in which said alkyl aluminum halide is dimethyl aluminum chloride.

10. The catalytic composite as set forth in claim 8 in which said alkyl aluminum halide is diethyl aluminum chloride.

11. The catalytic composite as set forth in claim 8 in which said alkyl aluminum halide is diethyl aluminum bromide.

12. The catalytic composite as set forth in claim 2 in which said aluminum halide is aluminum chloride.

13. The catalytic composite as set forth in claim 2 in which said aluminum halide is aluminum bromide.

14. The catalytic composite as set forth in claim 1 in which said porous support comprises alumina.

15. The catalytic composite as set forth in claim 1 in which said porous support comprises silica.

16. The catalytic composite as set forth in claim 1 in which said porous support comprises an aluminosilicate.

* * * * *